(12) United States Patent
Elnatan (10) Patent No.: US 10,143,606 B2
(45) Date of Patent: Dec. 4, 2018

(54) SIT-TO-STAND APPARATUS AND METHOD (71) Applicant: Debby Elnatan, Jerusalem (IL)

(72) Inventor: Debby Elnatan, Jerusalem (IL)

( * ) Notice: Subject to any disclaimer, the term of this patent is extended or adjusted under 35 U.S.C. 154(b) by 330 days.

(21) Appl. No.: 14/768,261

(22) PCT Filed: Feb. 13, 2014

(86) PCT No.: PCT/IL2014/050157
§ 371 (c)(1),
(2) Date: Aug. 17, 2015

(87) PCT Pub. No.: WO2014/125487
PCT Pub. Date: Aug. 21, 2014

(65) Prior Publication Data
US 2015/0359692 A1    Dec. 17, 2015

Related U.S. Application Data (60) Provisional application No. 61/765,054, filed on Feb. 15, 2013.

(51) Int. Cl.
*A61G 5/14* (2006.01)
*A61G 5/10* (2006.01)
(Continued)

(52) U.S. Cl.
CPC .............. *A61G 5/14* (2013.01); *A61F 5/3792* (2013.01); *A61G 5/1091* (2016.11); *A61G 5/12* (2013.01); *A61G 5/128* (2016.11); *A61H 3/04* (2013.01); *A63B 21/068* (2013.01); *A63B 21/4011* (2015.10); *A63B 21/4015* (2015.10); *A63B 23/0405* (2013.01); *A63B 69/0057* (2013.01);
(Continued)

(58) Field of Classification Search
CPC ....................................................... A61G 5/14
See application file for complete search history.

(56) References Cited

U.S. PATENT DOCUMENTS 4,948,156 A    8/1990   Fortner
4,985,947 A *  1/1991   Ethridge .............. A61G 7/1017
                                                       280/250.1
(Continued)

FOREIGN PATENT DOCUMENTS

CN    103169596    6/2013
EP    0237395      9/1987
(Continued)

OTHER PUBLICATIONS

Endorphin Sit to Stand Excerciser, accessed from the internet, http://www.endorphin.net/strength/330.
(Continued)

*Primary Examiner* — David R Dunn
*Assistant Examiner* — Tania Abraham
(74) *Attorney, Agent, or Firm* — Roach Brown McCarthy & Gruber, P.C.; Kevin D. McCarthy (57) ABSTRACT

An orthotic apparatus comprising: a seat; and a trunk support movable horizontally and vertically relative to said seat, said trunk support configured to confine motion of a user to a predetermined range when the user independently transitions between sitting on said seat and standing, and vice versa, so as to guide the user in the transition.

23 Claims, 5 Drawing Sheets

(51) Int. Cl.
*A61G 5/12* (2006.01)
*A63B 23/04* (2006.01)
*A63B 21/00* (2006.01)
*A63B 69/00* (2006.01)
*A63B 21/068* (2006.01)
*A61F 5/37* (2006.01)
*A61H 3/04* (2006.01)
*A63B 22/00* (2006.01)
*A63B 71/00* (2006.01)

(52) U.S. Cl.
CPC ..... *A63B 21/00181* (2013.01); *A63B 21/4035* (2015.10); *A63B 2022/0092* (2013.01); *A63B 2022/0094* (2013.01); *A63B 2071/0018* (2013.01)

(56) References Cited

U.S. PATENT DOCUMENTS

| | | | | |
|---|---|---|---|---|
| 5,346,280 | A * | 9/1994 | Deumite | A61G 5/14 180/907 |
| 5,701,968 | A * | 12/1997 | Wright-Ott | A61G 5/042 180/65.1 |
| 6,343,802 | B1 * | 2/2002 | Workman | A61H 3/008 135/67 |
| 6,733,018 | B2 | 5/2004 | Razon | |
| 6,770,040 | B2 * | 8/2004 | Perner | A61F 5/0102 482/124 |
| 6,832,770 | B1 * | 12/2004 | Wright-Ott | A47D 13/04 135/65 |
| 7,275,554 | B2 * | 10/2007 | Mullholand | A61H 3/008 135/67 |
| 7,601,104 | B2 | 10/2009 | Agrawal et al. | |
| 7,921,953 | B2 * | 4/2011 | Irvine | A61G 5/14 135/66 |
| 8,567,804 | B1 * | 10/2013 | Hoenhause | A61G 5/042 180/65.1 |
| 2005/0268397 | A1 * | 12/2005 | Nativ | A61G 7/1015 5/86.1 |
| 2010/0013276 | A1 | 1/2010 | Tholkes et al. | |
| 2011/0056019 | A1 * | 3/2011 | Altena | A61G 5/14 5/87.1 |
| 2012/0000496 | A1 | 1/2012 | Razon | |

FOREIGN PATENT DOCUMENTS

| | | |
|---|---|---|
| EP | 2401995 | 1/2012 |
| JP | 2012187284 | 10/2012 |
| WO | 9611658 | 4/1996 |
| WO | 2004056302 | 7/2004 |
| WO | 2012101574 A2 | 8/2012 |

OTHER PUBLICATIONS

Schenkman et al., "Whole-Body Movements During Rising to Standing from Sitting", Physical Therapy, Oct. 1990, vol. 70, No. 10: 638-648.

The NeuroGym Sit-to-Stand Trainer, accessed from the internet, http://www.neurogymtech.com/products/sit-to-stand-trainer.

* cited by examiner

SIT-TO-STAND APPARATUS AND METHOD

CROSS REFERENCE TO RELATED APPLICATIONS

This patent application is a U.S. National Phase filing of commonly owned PCT Application No. PCT/IL2014/050157, filed Feb. 13, 2014, which is based on and claims the benefit of the filing date of U.S. Provisional Patent Application Ser. No. 61/765,054, filed Feb. 15, 2013, both of which are incorporated herein by reference in their entirety.

FIELD OF THE INVENTION

The invention relates to the field of orthotics.

BACKGROUND

Daily standing in a standing device is an integral component in the rehabilitation protocol of those who suffer from gross motor dysfunction as a result of stroke, cerebral palsy, Parkinson's Disease, multiple sclerosis, traumatic head injury, etc. Many others suffer from disability resulting from muscle deterioration, spinal injuries, age, CMT (Charcot-Marie-Tooth disease), and more, and are limited even in routine daily activities. A large portion of this population finds themselves confined to a wheelchair with no professional rehabilitative care or ability to function independently.

Practicing the necessary daily repetitive movements and learning of gross motor skills, such as the transfer between sit to stand, standing, stand to sit and the like, usually require frequent physical therapy sessions. At present, other than in the hands of trained physiotherapists, persons with lower limb motor dysfunctions have limited possibilities for guided practice in the above rehabilitative activities at home. Repetition of these skills is necessary to optimize learning and to strengthen muscles and coordination for these specific actions.

Wheelchairs serve the need for mobility, while standers provide the essential daily vertical positioning. Neither device addresses the user's daily need to practice and acquire gross motor skills such as rising to standing, standing, and transferring to a seating position. For those persons with motor impairments who are dependent on daily supervision and caretaking, these basic skills are critical to lowering the caretaking burden. For those persons with motor impairments who are independent, these basic skills will determine their level of risk for falling accidents in and out of the home.

Sit-to-stand is one of the most common daily activities. It is a pre-requisite for other functional movements that require ambulation and is mechanically demanding. Sit-to-stand requires proper gross motor control, which is defined by the US National Library of Medicine as "the ability to make large, general movements (such as waving an arm or lifting a leg). It requires the proper integration of muscle, bones, and nerve function." Patients with gross motor dysfunction lack these abilities, and especially the sit-to-stand ability, that most of us take for granted. Gross motor dysfunction may be the result of numerous conditions. Some examples include cerebral palsy, stroke, Parkinson's disease, aging, spinal muscular atrophy, CMT (Peroneal Muscular Atrophy), TBI (Traumatic Brain Injury), muscular dystrophy, muscular sclerosis, partial spinal cord injury and more.

Devices for facilitating standing and sit-to-stand activities have been proposed.

U.S. Pat. No. 7,601,104 to Agrawal et al. discloses a passive gravity balancing assist device for human sit-to-stand motion. The design combines the use of auxiliary parallelograms with springs to produce an orthotic device wherein the total potential energy of the system is constant during standing and sitting motion.

PCT Publication No. WO2004/056302 to Ylva et al. discloses a human body supporting device, especially intended for use with children having serious functional disabilities, e.g. cerebral paresis. The device is characterized by comprising a base unit intended to rest on a horizontal ground, an elongated, generally up-right element extending from the base unit, a pelvis support attached to the upright element, said support being displaceable along the upright element, by said pelvis support comprising means for encircling the waist of the person using the device, and by a chest support provided on the upright element, said chest support being displaceable along the upright element and comprising means for encircling the chest of the person using the device.

European Patent No. 0237395 to Levasseur discloses an apparatus intended to permit the motorically handicapped to move in an upright position, by way of oscillation, to sit in a normal position or in an inclined position for relaxation, without help and without the provision of external energy. It consists of a framework bearing support breeches in which the user is suspended by the pelvis, held on a back part by struts, his inanimate legs being positioned in a support integral with a collapsible seat. Two pairs of lateral articulated legs allow the user to move by displacement of the centre of gravity of the assembly beyond the bearing point of the legs positioned to the front, by pushing on walking sticks, for example. Two operating handles and allow the desired position to be adopted (standing, inclined for relaxation, seated).

PCT Publication No. WO1996/11658 to Misako discloses a posture change system and a posture change method which are capable of being applied to a wide range of patients. The posture change system includes a frame with casters. The frame comprises an arm rocked by a screw driven mechanism, a pair of knee pads and a level-adjustable foot rest plate. The arm is composed of upper and lower rods extending parallel to each other. These rods cooperate with each other to form a parallelogram link. Rocking centers of the arm are positioned at the level of the abdominal portion of the patient in a sitting posture. To the arm is attached a slide means which is slidably movable in the direction which the arm extends. A hook is provided on a slider which defines a part of the slide means. In addition, a hook is provided on a bent forward chest pad attached to the tip end of the arm. A sling mounted on the patient is attached to the system by engaging its upper arm portions with the hook of the chest pad and engaging its lower arm portions with the hook of the slider, whereby the patient is united with the system.

U.S. Pat. No. 5,701,968 to Wright-Ott et al. discloses a multi positioning power mobility aid for physically challenged children is provided. The power mobility aid provides a transition to a power wheelchair. The power mobility aid includes a multi positioning main frame that allows a child to be placed in a sitting, semi-standing or standing position without requiring multiple adjustments. The back support rotates to a non supporting position to facilitate placing a child in or removing a child from the power mobility aid. The back support then locks into an upright supporting position after the child is positioned in the power mobility aid. The power mobility aid includes an adjustable arm that supports the user-operable input device in multiple locations.

U.S. Patent Application Publication No. 2010/0013276 to Tholkes et al. discloses a modular standing frame. The modular standing frame has a chair module adapted to raise and lower a user between sitting and standing postures without inducing shear between the user and the seat and seat back of the chair module. The chair module may be selectively coupled to one of a glider module adapted to provide walking-type exercise to a standing user, a workstation module that provides a work surface for a sitting or standing user, and a mobility module that allows the standing frame to be moved about by a user much like a wheel chair.

The NeuroGym Sit-to-Stand Trainer, sold by NeuroGym Technologies, Inc. of Ottawa, Ontario, Canada, uses a counter-weight mechanism to provide a way to strengthen weight-bearing muscles and increase standing stability and endurance. The Sit-to-Stand Trainer enables an individual to actively initiate the motion of standing up, even with weakened or seemingly unsuccessful efforts. See http://www.neurogymtech.com/products/sit-to-stand-trainer, last accessed Jan. 27, 2013.

The Endorphin STS, sold by Endorphin Corp. of Pinellas Park, Fla., is a sit to stand exerciser that is designed to assist the user in sitting and standing independently. Based on the user's body weight and ability, the closed chain assistance load is decreased incrementally until the patient can perform the exercise without assistance. See http://www.endorphin.net/strength/330, last accessed Jan. 27, 2013.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, an orthotic apparatus comprising: a seat; and a trunk support movable horizontally and vertically relative to said seat, said trunk support configured to confine motion of a user to a predetermined range when the user independently transitions between sitting on said seat and standing, and vice versa, so as to guide the user in the transition.

There is further provided, in accordance with an embodiment, an orthotic apparatus comprising: a seat; and a trunk support, wherein the orthotic apparatus is characterized in that: (a) said trunk support is movable horizontally and vertically relative to said seat, and is prevented from moving laterally relative to said seat, and (b) said orthotic apparatus does not apply any force to aid the user in standing up from said seat, such that the user independently transitions between sitting on said seat and standing.

In some embodiments, independently comprises the user bearing the majority of a body weight of the user during the transition.

In some embodiments, the orthotic apparatus further comprises a weight compensator configured to compensate for a weight of said trunk support, so as to minimize interference of said trunk support with the transition of the user.

In some embodiments, the orthotic apparatus further comprises one or more handles positioned forward of the seat, to guide the user to bring a center of gravity of the user forward during the transition.

In some embodiments, said one or more handles are positioned at a height forcing the user to release a grip on said one or more handles during a body extension phase.

In some embodiments, said one or more handles are positioned at a height enabling the user to maintain a grip on said one or more handles during an entirety of the transition.

In some embodiments, said trunk support is further configured to cushion a fall of the user from standing to sitting.

In some embodiments, said seat is further configured to cushion a fall of the user from standing to sitting.

In some embodiments, the orthotic apparatus further comprises one or more footrests configured to secure one or more feet of the user, respectively.

In some embodiments, the orthotic apparatus further comprises one or more calf supports configured, together with said one or more footrests, to maintain the ankle and calf of each leg of the user in same sagittal planes, and the two legs being in parallel sagittal planes during the STS transitions.

In some embodiments, said one or more footrests are further configured to slide backwards upon a beginning of the transition between sitting on said seat and standing, thereby making the user enter a posture suitable for a flexion momentum phase of the transition between sitting on said seat and standing.

In some embodiments, said seat is further configured to slide forward upon a beginning of the transition between sitting on said seat and standing, thereby making the user enter a posture suitable for a flexion momentum phase of the transition between sitting on said seat and standing.

In some embodiments, the orthotic apparatus further comprises a set of wheels for mobilizing the orthotic apparatus.

In some embodiments, said set of wheels comprises user-propelled wheels.

In some embodiments, the orthotic apparatus further comprises a motor configured to propel at least one wheel of said set of wheels.

In some embodiments, said trunk support comprises: a trunk column; and a trunk harness attachable to the user and connected to said trunk column along a height of at least a portion of a trunk of the user.

In some embodiments, said trunk harness is connected to said trunk column at a waist level of the user and at an armpit level of the user.

In some embodiments, said trunk harness is further connected to said trunk column at a pelvis level of the user.

In some embodiments, said trunk support further comprises a fixation mechanism configured to affix the user in a standing posture.

There is further provided, in accordance with an embodiment, a combined chair and dynamic stander for use by a motorically-limited user, the apparatus comprising: a seat; a trunk support movable horizontally and vertically relative to said seat, said trunk support configured to confine motion of a user to a predetermined range when the user independently transitions between sitting on said seat and standing, and vice versa, so as to guide the user in the transition; and a set of wheels for mobilizing the combined chair and dynamic stander.

In some embodiments, the combined chair and dynamic stander further comprises a weight compensator configured to compensate for a weight of said trunk support, so as to minimize interference of said trunk support with the transition of the user.

In some embodiments, the combined chair and dynamic stander further comprises one or more handles positioned forward of the seat, to guide the user to bring a center of gravity of the user forward during the transition.

In some embodiments, said one or more handles are positioned at a height forcing the user to release a grip on said one or more handles during a body extension phase.

In some embodiments, said one or more handles are positioned at a height enabling the user to maintain a grip on said one or more handles during an entirety of the transition.

In some embodiments, said trunk support is further configured to cushion a fall of the user from standing to sitting.

In some embodiments, said seat is further configured to cushion a fall of the user from standing to sitting.

In some embodiments, the combined chair and dynamic stander further comprises one or more footrests configured to secure one or more feet of the user, respectively.

In some embodiments, the combined chair and dynamic stander further comprises one or more calf supports configured, together with said one or more footrests, to maintain vertical alignment of a calf and an ankle of each leg of the user.

In some embodiments, said one or more footrests are further configured to slide backwards upon a beginning of the transition between sitting on said seat and standing, thereby making the user enter a posture suitable for a flexion momentum phase of the transition between sitting on said seat and standing.

In some embodiments, said seat is further configured to slide forward upon a beginning of the transition between sitting on said seat and standing, thereby making the user enter a posture suitable for a flexion momentum phase of the transition between sitting on said seat and standing.

In some embodiments, said set of wheels comprises user-propelled wheels.

In some embodiments, the combined chair and dynamic stander further comprises a motor configured to propel at least one wheel of said set of wheels.

In some embodiments, said trunk support comprises: a trunk column; and a trunk harness attachable to the user and connected to said a trunk column along a height of at least a portion of a trunk of the user.

In some embodiments, said trunk harness is connected to said a trunk column at a waist level of the user and at an armpit level of the user.

In some embodiments, the combined chair and dynamic stander is further configured to serve as a passive stander, wherein said trunk support further comprises a fixation mechanism configured to affix the user in a standing posture.

There is yet further provided, in accordance with an embodiment, a therapeutic method for training a motorically-limited user in free standing, in sit-to-stands transitions and in stand-to-sit transitions, the method comprising: providing an orthotic apparatus comprising a seat and a trunk support, wherein said trunk support is movable horizontally and vertically relative to said seat; and using the orthotic apparatus, confining motion of the user to a predetermined range when the user independently transitions between sitting on said seat and standing, and vice versa, so as to guide the user in the transition.

In some embodiments, the predetermined range comprises a lateral predetermined range, to prevent the user from falling sideways.

In some embodiments, the predetermined range comprises a limitation of a forward motion of the user, to prevent the user from falling forward when standing.

In some embodiments, the method further comprises adjusting the predetermined range by adjusting the apparatus.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Disclosed herein are an orthotic apparatus, a combined apparatus of a chair and a dynamic stander for use by a motorically-limited user, and a therapeutic method for training a motorically-limited user in free standing, in sit-to-stands transitions and in stand-to-sit transitions.

Advantageously, the present apparatuses and method enable the motorically-limited user to perform sit-to-stand and stand-to-sit transitions (hereinafter jointly referred to as "STS") on his or her own, without requiring external power—such as another person, a motor, a weights mechanism, springs etc. Nonetheless, the apparatuses do allow a mode in which external assistance to the STS transition is provided. For example, the apparatus may be equipped with means for pushing and/or pulling the user from a sitting position to a standing position. The means may include a manual pulley system, a pneumatic system, an electrical system and/or the like, operable by a caregiver and/or by the user.

Many existing STS devices require external power to function, posing increased risk to the user and necessitating supervisory staff for safe use. Additionally, many such devices only move the user through predetermined movement patterns rather than allowing the user to move under his or her own initiative, control, and muscle power. Advantageously, the present apparatuses and method do allow the user to experience and practice appropriate movement, thus facilitating changes in the nervous system to promote the learning or relearning of typical patterns. Moreover, the present apparatus and method permit the user to experience his or her full weight bearing, which is necessary to develop the muscle power and strength for independent standing and to maintain and increase bone density. The user develops strength and coordination subjectively, relative to his or her body weight.

In addition, the present device and method teach and encourage the user to eventually stand up without needing to use their hands in any way to pull or push themselves up into standing, a method commonly used to make up for muscle weakness. This teaching and encouragement is done by reducing the user's dependence on their hands, using the adjustable handles.

The present apparatuses and method are suitable, inter alia, for persons suffering from motor neuron diseases, such as amyotrophic lateral sclerosis (ALS), primary lateral sclerosis (PLS), progressive muscular atrophy (PMA), progressive bulbar palsy (PBP) or pseudobulbar palsy. Those suffering from other gross motor dysfunctions may also benefit from the apparatuses and method; such dysfunctions may include, for example, cerebral palsy, stroke, Parkinson's disease, aging, spinal muscular atrophy (SMA), Charcot-Marie-Tooth disease (CMT), TBI (Traumatic Brain Injury), muscular dystrophy, muscular sclerosis, partial spinal cord injury and more. The apparatuses and method may be adjunct to professional rehabilitation activities, such as gross motor physical therapy, postural management, occupational therapy etc.

In some embodiments, the apparatuses are multi-functional, serving both as a chair, as a passive (fixed) stander and as a dynamic (enabling STS) stander. When in a passive stander mode, the apparatus may lock one or more joints of the user at a fixed horizontal and/or vertical position, or limit motion of these joints to a predefined horizontal and/or vertical range, optionally of a few centimeters (e.g. up to 10 centimeters). Optionally, the apparatuses include wheels for enabling indoors and outdoors mobility, and are sufficiently narrow to pass through most standard doors. Further optionally, the apparatuses are highly-accessible from the front, enabling the user to participate in ordinary upright and sitting activities. A seat cushion of the apparatuses may be easily exchangeable with a toilet seat or a potty, so that the user need not be removed from the apparatuses to use the bathroom.

The apparatuses provide for orthopedically-safe STS transitions. Although the user, according to some embodiments, performs the transition independently, the apparatuses still confine him or her to a predetermined range of motion that can be custom set for each user according to their abilities, thereby enhancing safety. The confinement is to one or more of the following limitations: lateral limitation, to prevent the user from falling to one of the sides during STS transitions; and frontal limitation, to prevent the user from falling forward after reaching a standing posture.

The term "independently", as referred to herein with regard to an STS transition, may relate to the fact that the apparatuses do not, in some embodiments, apply any force to aid the user in standing up. Namely, the user may stand up solely using his or her own muscle power.

In addition, the sitting posture of the user is, naturally, confined by the seat of the chair (and the trunk support), which are optionally padded to provide for shock absorption and a comfortable, protected fall from standing to sitting. The protected fall helps in training the user how to stand, similar to a typical healthy child development, in which falling is part of the learning curve. When a typical child learns how to stand, he or she receives real-time feedback during the process: if the process of sit-to-stand is successful, the child finds himself or herself standing; if not, the child falls to crouch or to the ground. Later in the process, when the child learns how to remain standing, positive feedback is received when succeeding to stand for longer spurts, and negative feedback is received when fatigue causes the child to collapse into crouching or onto the ground. Similarly, in the present apparatuses and method, the user also receives real-time feedback on the STS transition and on maintaining the standing posture: If the user is successful in the sit-to-stand transition, he or she successfully rises to stand. If not, they safely fall back to a seating position. When the user attempts to maintain the standing position, the success is dependent only on his or her abilities; success means that the user can stand for longer spurts, while failure means that the user collapses, safely, onto the chair. Falling, under present embodiments, is the natural feedback to weakness, poor balance and/or lack of sufficient coordination.

Accordingly, a multifunctional home-based solution, serving as a chair, dynamic stander and passive stander, enabling its user to acquire and practice motor skills independently, can significantly improve quality of life—not only for its intended users, but also for the person's caretakers. Such a device reduces the need for strenuous multiple transfers between standers, wheelchairs and other training devices during the day. In the medical literature, it is acceptable to divide the sit-to-stand transition into four phases. See, for example, M. Schenkman, R. A. Berger, P. O'Riley, R. W. Mann and W. A. Hodge, *Whole-Body Movements During Rising to Standing from Sitting*, Physical Therapy, October 1990, vol. 70, no. 10: 638-648, which is incorporated herein by reference. Phase I is often referred to as the flexion-momentum phase, in which the initial momentum for rising is generated. In this phase, the trunk's center of gravity starts moving forward, in preparation for standing. During this motion, the angle between the trunk and the thighs, as well as the angle between the thighs and the calves, decreases. The decreasing of the angle between the thighs and the calves is achieved either by sliding the feet backwards or by sliding the thighs and buttocks forward—or both. The phase ends just before the buttocks are lifted off the seat, when the knee is already horizontally forward of the ankle joint.

Phase II is referred to as the momentum transfer phase. Is begins when the user leaves the seat and ends when the user is at a partial squat, at maximum ankle dorsi-flexion. During this phase, the forward momentum of the upper body is transferred to a forward and upward momentum of the entire body.

Phase III, referred to as the extension phase, is initiated just after maximal ankle dorsi-flexion is completed. Angles between the trunk and thighs, as well as between the thighs and calves, continue to increase. Then, in Phase IV, often called the stabilization stage, the body has reached its full upright position and is stabilized in a standing position.

Advantageously, the present apparatuses and method are designed to guide the user's transition between the four phases, using solely his or her own muscle power, and to protect the user from physical harm during the transition, as discussed above.

Figure 1A:
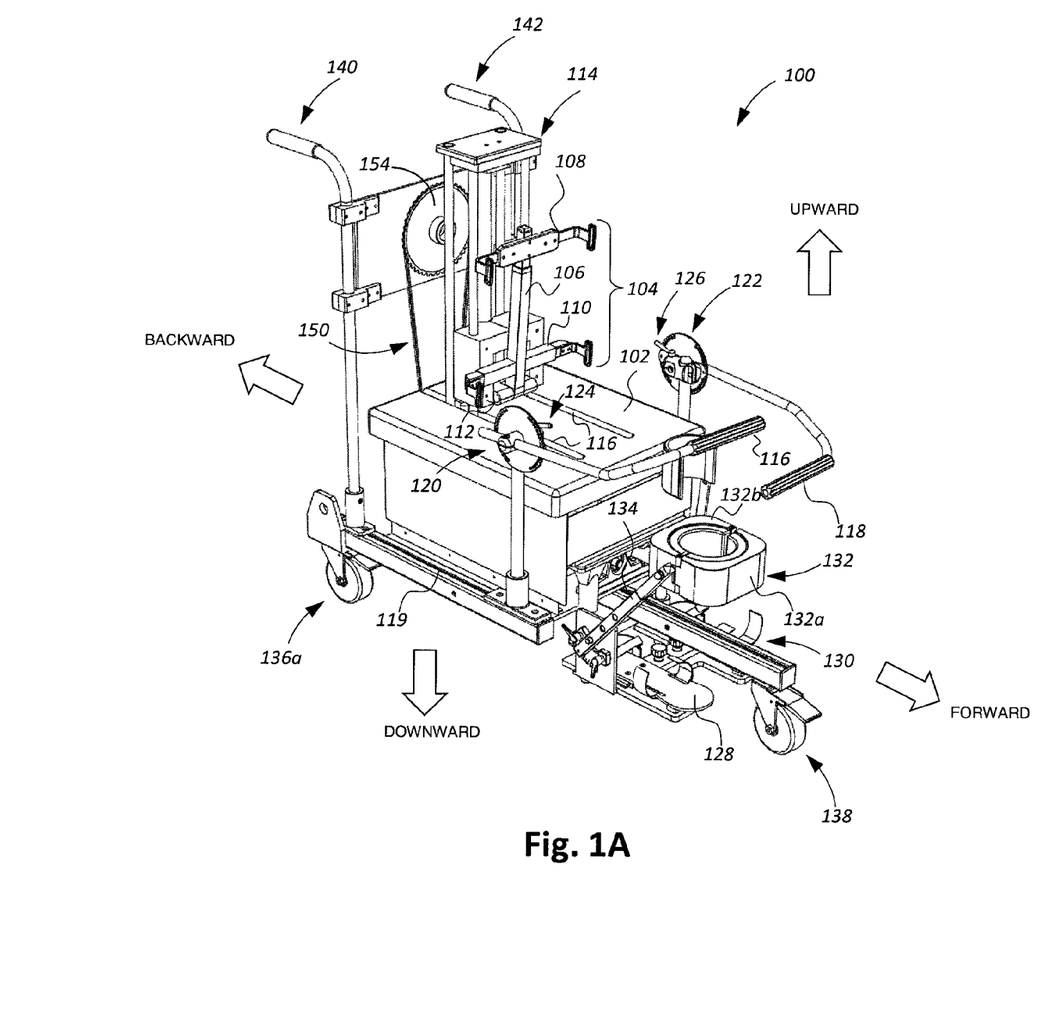
FIG. 1A shows a front perspective view of an exemplary orthotic apparatus, which may also serve as a combined apparatus of a chair and a dynamic stander for use by a motorically-limited user.
Figure 1B:
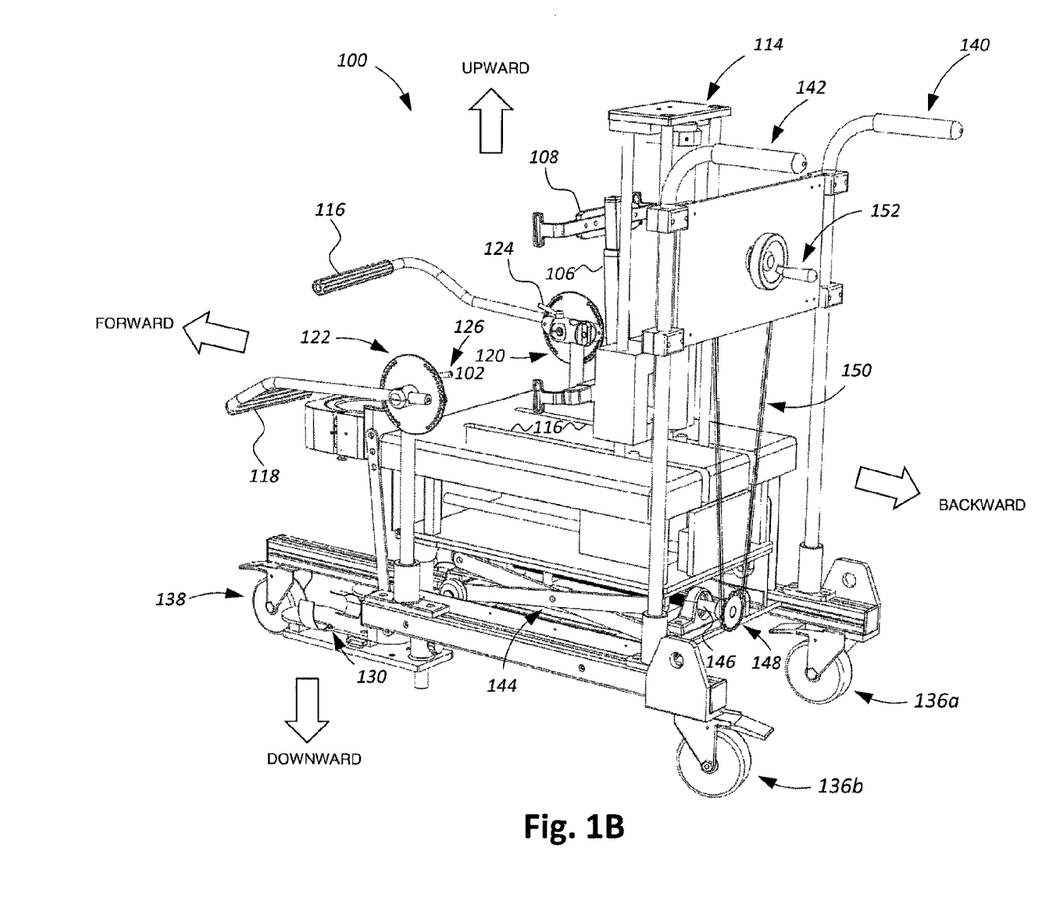
FIG. 1B shows a rear perspective view of the apparatus of FIG. 1A.

Reference is now made to FIGS. 1A and 1B, which show front and back perspective views, respectively, of an exemplary STS apparatus 100 (also referred to as an "orthotic apparatus", a "combined chair and dynamic stander" or simply "apparatus"), in accordance with some embodiments.

Apparatus 100 may include a seat, such as seat 102, and a trunk support, such as trunk support 104—which is, in this example, an optionally telescopic trunk column 106 and two harness holders: a top harness holder 108 and a bottom harness holder 110. A trunk harness (not shown) may be attached to a user of apparatus 100, and connected to top and bottom harness holders 108 and 110, respectively. The trunk harness and trunk support 104 may be so configured to connect the user to apparatus 100 along a height of at least a portion of the trunk of the user. This portion, optionally, starts at the user's hip joint level and above, so as to connect the user's trunk securely to the trunk support 104 during the STS transition and while standing.

The harness may include multiple straps and/or a vest. The harness may secure the user at the crotch, waist, armpits and/or shoulders. Crotch securing may ensure that the harness does not move upwards relative to the user. Shoulder securing may ensure that the harness does not move downwards relative to the user.

A different trunk support (not shown) may include a different number of harness holders, which may be differently-positioned. For example, the trunk support may include a shoulders harness holder, a mid-trunk harness holder and a pelvic harness holder—the latter being configured to connect to a harness securing the user's pelvic area.

Support at the pelvic level ensures that the user's pelvis is secured and substantially centered symmetrically onto trunk support 104 during STS, and cannot slide forward, bringing the user into a slumped position, during sitting. Additionally, it ensures that the two hip joints cannot protrude while standing more forward than the user's two ankle joints, at least not substantially.

Support at the waist and optionally up to the armpit level ensures that the user's trunk is secured onto the trunk support 104 during STS so that users who have a lack of trunk control during STS can practice STS in a substantially symmetrical manner and safely within the predetermined range of movement for that user. The support above the waist level, which is optionally up to about the armpit level of the user, ensures that when the standing momentum of the user is stopped by the waist level support, the user's upper parts (trunk, head, etc.) do not continue the motion and fall forward of the waist. If column 106 is telescopic, adjustments may be made to the levels of connection of the user to trunk support 104.

Trunk support 104, advantageously, is configured to confine motion of a user to a predetermined range when the user independently transitions between sitting on seat 102 and standing, and vice versa, so as to guide the use in the transition and to avoid excessive trunk movement forward, backward and laterally.

Trunk support 104 is optionally movable horizontally and vertically relative to seat 102, and optionally also pivotally about a hinge, such as hinge 112. Trunk support 104 is optionally prevented from moving laterally relative to seat 102, namely perpendicularly to the sagittal plane of the user. The term "horizontally" refers to movement forward (generally where the user is facing) and backward (generally opposite to where the user is facing), as indicated by arrows in the figure, which is in parallel to the sagittal plane of the user. The term "vertically" refers to movement upwards and downwards, which is also in parallel to the sagittal plane of the user. Since seat 102 is configured for receiving a user such that the user is facing forward, reference is made here to horizontal and vertical motion which is relative both to the seat and to the user.

In a different embodiment (not shown), a trunk support allows lateral movement of the user but only to a limited range, such as a few centimeters up to a few dozen centimeters sideways. For example, such trunk support may be configured to allow lateral movement of up to 10 centimeters sideways. As another example, such trunk support may be configured to allow lateral movement of up to 15 centimeters sideways.

Optionally, a weight compensator 114, in the form of an essentially vertical pillar, may be included in apparatus 100. Weight compensator 114 may compensate for gravitational forces acting on trunk support 104, so as to minimize interference of the trunk support with the transition of the user. That is, the self weight of trunk support 104 and optionally that of the harness (not shown), may make the user's STS transition more difficult and not truly correlated with his or her body weight. Accordingly, weight compensator 114 may include one or more weights (not shown), pulling trunk support 104 up via a pulley (not shown) positioned at the top of the weight compensator. The pulling force may be adjusted, for example by connecting and disconnecting individual weights from a cable (not shown), so as to match the force to the weight of trunk support 104 and optionally of the harness.

Optionally, apparatus 100 may include a handle which, when pulled or otherwise suitably manipulated by a caregiver, pulls the user upwards and optionally forwards, to bring him or her to a standing position. This handle may either be part of weight compensator 114 or be separate.

To these ends, trunk support 104 may be mounted on a vertical trunk support column (or "trunk column" for short) 114, optionally via hinge 112. Trunk column 114 may extend to below the level of seat 102, where is connects to a horizontal track (not shown), allowing it to slide horizontally—forward and backward. One or more slits, such as two slits 116, may be provided in seat 102, to allow for the motion of trunk column 114 through the seat. Optionally, trunk column 114 is telescopic, namely—it includes multiple sections collapsible into one another, enabling the trunk column to extend and contract in length.

Optionally, trunk support 104 includes a vertical fixation mechanism (not shown) configured to affix the user in a standing posture. The fixation mechanism may affix trunk support 104 at least in the vertical axis, namely—secure the trunk support to trunk column 114 at a height which fits the user's standing position, to prevent the user's from collapsing into crouching. Further fixation may be done at the horizontal axis, affixing trunk column 114 during passive standing to the horizontal track (not shown) which lies below seat 102, thereby preventing the user's trunk from moving backwards. Finally, fixation or a predetermined allowable trunk flexion angle may also be made at hinge 112. Fixation of hinge 112 secures the user's trunk in a vertical axis, giving the weak or tired user trunk support during sitting and during passive standing. Predetermining an allowable trunk flexion angle at hinge 112 permits tailoring the apparatus 100 to each user's individual needs and capabilities, enabling each user to develop trunk control during STS at their own level and rate. Vertical fixation may be achieved by predetermining an allowable trunk flexion angle, by delimiting the forward pivot of hinge 112 beyond a certain angle.

Apparatus 100 may further include one or more handles, such as a right handle 116 and a left handle 118, positioned forward of seat 102. Handles 116 and 118, advantageously, may guide the user to bring his or her center of gravity forward during a sit-to-stand transition. To achieve this, the position of handles 116 and/or 118 may be set such that they are located slightly forward of the user's reach when fully seated. The position of handles 116 and/or 118 may be adjustable, for example by sliding along a rail 119 and/or through a suitable aperture in each of handle hinge systems 120 and 122. After the user moves his or her center of gravity forward to grip handles 116 and/or 118 and starts to rise, the handles may also move up, by virtue of handle hinge systems 120 and 122, respectively. Each of handle hinge systems 120 and 122 may include a friction mechanism, such as a ball-and-socket mechanism, to maintain the position of handles 116 and 118 when the user releases them. Optionally, the friction mechanism and/or a different mechanism may enable securing handles 116 and/or 118 at a certain angle, so that they do not move even if the user applies force on them. For example, fixation handles 124 and 126 may be used to affix handles 116 and 118, respectively, at a desired angle.

Affixing handles 116 and/or 118 at a certain angle may be beneficial, for example, in order to position them at a height which forces the user to release his or her grip on them when rising, during a body extension phase. This ensures that, on one hand, handles 116 and/or 118 are available to induce the user to move his or her weight forward, but on the other hand, not to completely rely on the handles for the entire sit-to-stand transition.

To cushion and absorb the shock of the user's fall from standing to sitting, one or more configurations are provided: As a first example, seat 102 may simply be padded.

As another example, trunk support 104 may include a deceleration mechanism (not shown) which decelerates the motion of the trunk support downwards, as the user approaches seat 102. The deceleration mechanism may be, for example, a pneumatic or hydraulic mechanism, which is configured to decelerate the motion of trunk support 104 only downwards, at a pre-determined range of motion above seat 102. As another example, weight compensator 114 may include a deceleration mechanism (not shown) which decelerates the motion of trunk support 104 downwards on trunk column 106 and/or backwards on the horizontal rail(s), as the user approaches the end of the vertical/horizontal range, respectively.

Apparatus 100 may further be provided with one or more footrests, such as a right footrest 128 and a left footrest 130, configured to secure one or more feet of the user, respectively. The position of each of footrests 128 and/or 130 may be adjusted in one, two or three dimensions.

To guide the user in a sit-to-stand transition, and specifically in the flexion-momentum phase, seat 102 and footrests 128 and/or 130 may be movable relative to each other during this phase. For example, seat 102 may be configured to slide forward. Additionally or alternatively, footrests 128 and/or 130 may be configured to slide backward.

Calf supports, such as a right calf support 132 and/or a left calf support (not shown) may be provided in apparatus 100, to maintain, together with footrests 128 and/or 130, the ankle and calf of each leg of the user in the same sagittal planes, and the two legs being in parallel sagittal planes during the STS transitions. This prevents the knees from collapsing externally or internally during the transitions. Each calf support, such as right calf support 132, may be formed, for example, as a pair of braces 132*a-b*, connected to an optionally telescopic shaft 134, whose base is affixed relative to footrest 128.

Optionally, one or more of the calf supports are connected to respective sides of trunk support 104 and/or to respective sides of a pelvic harness, if one exists. The connection may be, for example, via two rigid shafts pivotally connected to one another; one shaft being disposed parallel to the user's thigh and the other parallel to the user's upper calf. These connections may form what is known as an "exoskeleton".

Apparatus 100 may further include a set of wheels for its mobilization. Merely as an example, apparatus 100 may include three wheels, two 136*a-b* at the back and one 138 at the front. One or more of wheels 136-138 may be a swivel caster, optionally equipped with a stopper.

Alternatively, if the user has good control over his or her hands and sufficient muscle power, an apparatus similar to apparatus 100 may be equipped with a wheelchair-like wheel configuration (not shown), for example two large, user-propelled wheels at the back, and one or more smaller wheels at the front.

With either alternative, apparatus 100 may include one or more motors configured to propel at least one wheel of the set of wheels. Additionally or alternatively, push handles, such as handles 140 and 142, may be provided at the back of apparatus 100, to enable another person to assist in mobilization of the apparatus.

Apparatus 100 may further include a height adjustment mechanism, to adjust the height of seat 102 and optionally other elements of the apparatus for different needs. For example, height adjustment is beneficial for allowing a child to stand close to the floor on one hand, but sit comfortably at the family table of the other hand. Similarly, height adjustment may be applied to users of different body heights. The height adjustment mechanism may include, for example, a jack 144, which is extendible and collapsible by virtue of an elongated screw 146, rotatable using a system of a bottom gear 148, and interconnecting chain 150 and an upper gear 154. Upper gear is 154 rotatable using a handle 152, conveniently positioned at approximately waist-level of the caregiver.

Apparatus 100 may include one or more sensors (not shown) for tracking and metering the usage of the apparatus by the user. The output of the sensors may be used by a computerized controller (not shown), which is either a part of apparatus 100 or external to it, in order to analyze the usage and derive data which may assist in further training of the user. Additionally or alternatively, apparatus 100 may be equipped with one or more electric muscle stimulators (not shown), controlled by the same computerized controller or a different one, for stimulating muscles before and/or during an STS transition. Timed, sequential muscle stimulations may further assist the user in the STS transition.

Figure 2:
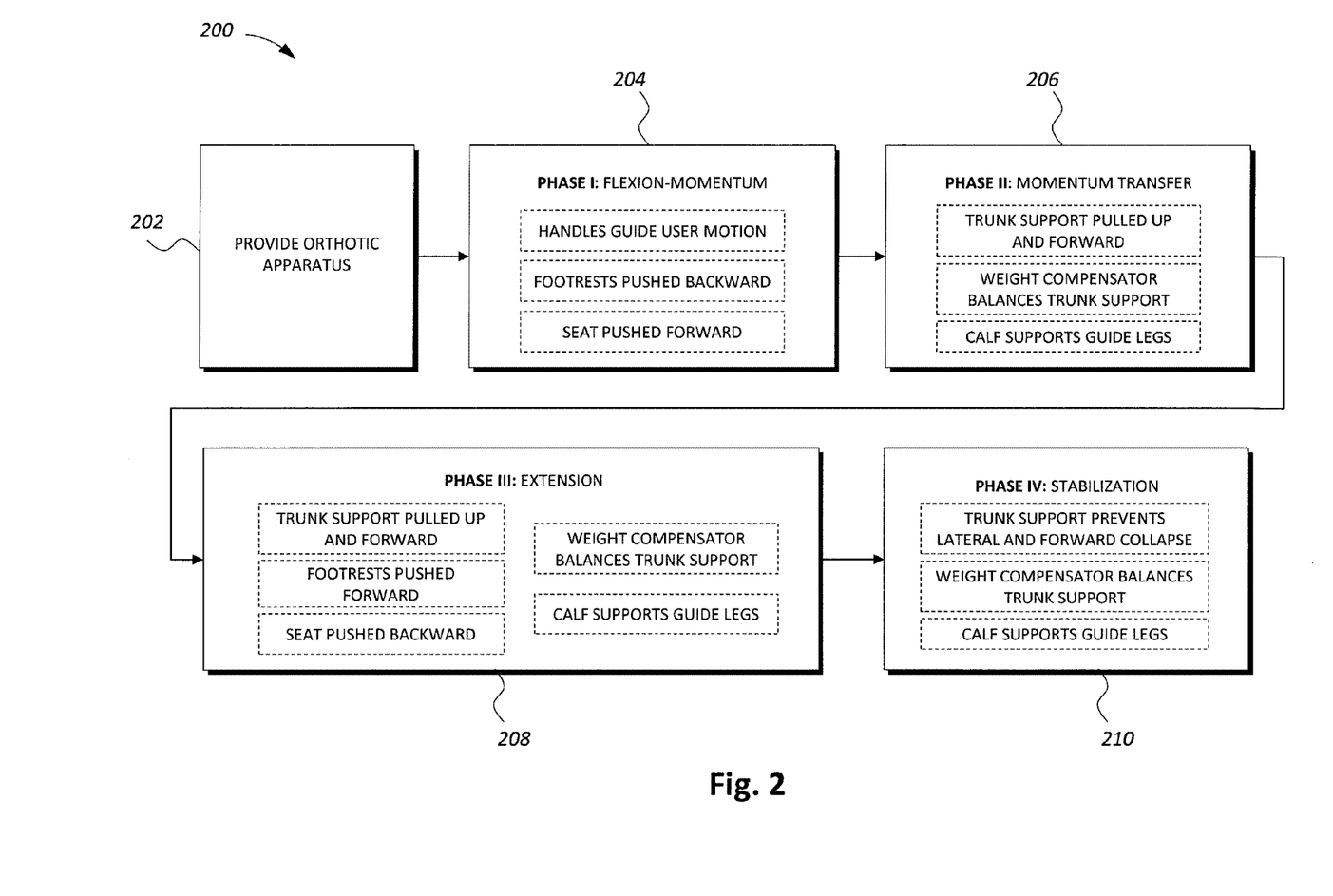
FIG. 2 shows a flow chart of an exemplary therapeutic method for training a motorically-limited user in free standing, in sit-to-stands transitions and in stand-to-sit transitions.

A therapeutic method, in accordance with some embodiments, may include providing an orthotic apparatus having a seat and a trunk support—such as apparatus 100 of FIGS. 1A-B. Then, using the apparatus, motion of the user is confined to a predetermined range when the user independently transitions between sitting on the seat and standing, and vice versa, so as to guide the user in the transition. Reference is now made to FIG. 2, which shows, in greater detail, a flow chart of an exemplary therapeutic method 200 for training a motorically-limited user in free standing, in sit-to-stands transitions and in stand-to-sit transitions.

In a step 202, an orthotic apparatus, such as apparatus 100 of FIGS. 1A-B, is provided. In a step 204, the apparatus facilitates the flexion-momentum phase of the sit-to-stand transition, as follows: the one or more footrests of the apparatus are pushed backwards by the user, and/or the seat of the apparatus is pushed forward by the user. The hinge of the trunk support allows the user to bend his or her trunk forward while reaching out to at least one of the handles.

In a step 206, the apparatus facilitates the momentum transfer phase of the sit-to-stand transition, as follows: The trunk support confines the independent motion of the user's trunk to a predetermined range laterally and optionally also forward and backwards, such that the user's center of mass does not cause the apparatus to topple forward, backwards or to the sides despite the forces and momentum applied to the device. The optional weight compensator negates the weight of the trunk support and optionally of the harness, so as not to burden the user with any weight in addition to his or her own body weight. The calf supports ensure that the legs of the user can move forward and backwards in a sagittal plane above the ankle, and that the knees do not collapse internally or externally.

In a step 208, the apparatus facilitates the extension phase of the sit-to-stand transition, as follows: The trunk support continues to confine the independent motion of the user to a predetermined range, laterally and optionally also forward, as discussed above. The optional weight compensator continues to negate the weight of the trunk support and optionally of the harness. The calf supports continue to ensure that the legs of the user can move only forward and backwards in the sagittal plane above the ankle. Optionally, the seat only returns to its original position when the user sits down.

Finally, in a step 110, the apparatus facilitates the stabilization phase of the sit-to-stand transition, as follows: The trunk support continues to confine the independent motion of the user to a predetermined range laterally, and optionally forward and backwards, as discussed above. The optional weight compensator continues to negate the weight of the trunk support and optionally of the harness. The calf supports continue to ensure that the legs of the user cannot collapse internally or externally.

Figure 3:
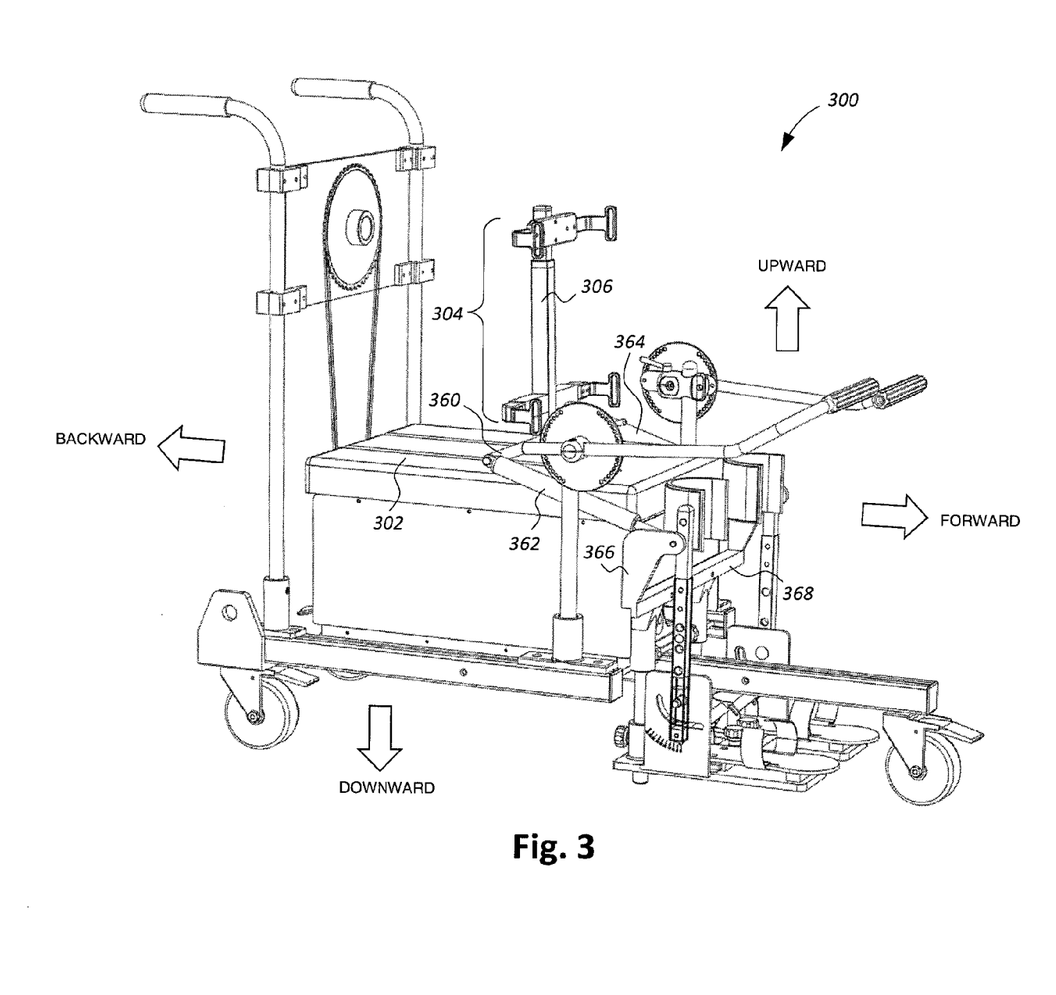
FIG. 3 a front perspective view of an exemplary orthotic apparatus, which may also serve as a combined apparatus of a chair and a dynamic stander for use by a motorically-limited user.

Reference is now made to FIG. 3, which show a front perspective view of an exemplary STS apparatus 300 (also referred to as an "orthotic apparatus", a "combined chair and dynamic stander" or simply "apparatus"), in accordance with an alternative embodiment. Apparatus 300, in this embodiment, may include essentially the same elements of apparatus 100 (FIGS. 1A-B) and operate in accordance with the same principles of method 200 (FIG. 2), except with regard to those specific elements and principles discussed below as being different. For reasons of simplicity, elements of apparatus 300 which are identical to corresponding elements of apparatus 100 (FIGS. 1A-B), are not numbered in FIG. 3. In addition, it is explicitly intended that all of the above discussions will apply, mutatis mutandis, to apparatus 300.

Apparatus 300, different from apparatus 100 (FIGS. 1A-B), may use different means for confining motion of a user to a predetermined range when the user independently transitions between sitting and standing, and vice versa, so as to guide the use in the transition and to avoid excessive trunk movement forward, backward and laterally. Instead of having a trunk column (e.g. 114 in FIGS. 1A-B which extends to below the level of a seat 302, where is connects to a horizontal track, a trunk support 304 of apparatus 300 includes a polar fixation mechanism.

The polar fixation mechanism may include an interconnection between trunk column 306 and a base or a chassis of apparatus 300. This interconnection may be achieved, for example, as follows: A horizontal shaft 360 may be secured to a bottom area of trunk column 306, for example through a hole in the bottom area. Horizontal shaft 360 may be pivotally connected, at each of its ends, to a telescopic lateral shaft—lateral shaft 362 on the right and lateral shaft 364 on the left. In the alternative, it is also possible (this option is not shown) to connect horizontal shaft 360 to only one lateral shaft, on only one side. Each of lateral shafts 362 and 364 may be pivotally connected to a base or a chassis of apparatus 300. As one example, this connection is via a connection member 368 extending over the width of a base of apparatus 300, wherein the connection member has a pair of flanges (only a right flange 366 is shown). Lateral shaft 362, for example, may be pivotally connected to flange 366.

In another embodiment (not shown), a polar fixation mechanism may be configured differently. For example, the polar fixation mechanism may include a different number of shafts, pivots and/or connections compared to apparatus 300. The principle is that the trunk support can move forward and backward, upward and downward, in relation to a base or a chassis of the apparatus, but physically prevents lateral movement which may cause the user to fall sideways.

Figure 4:
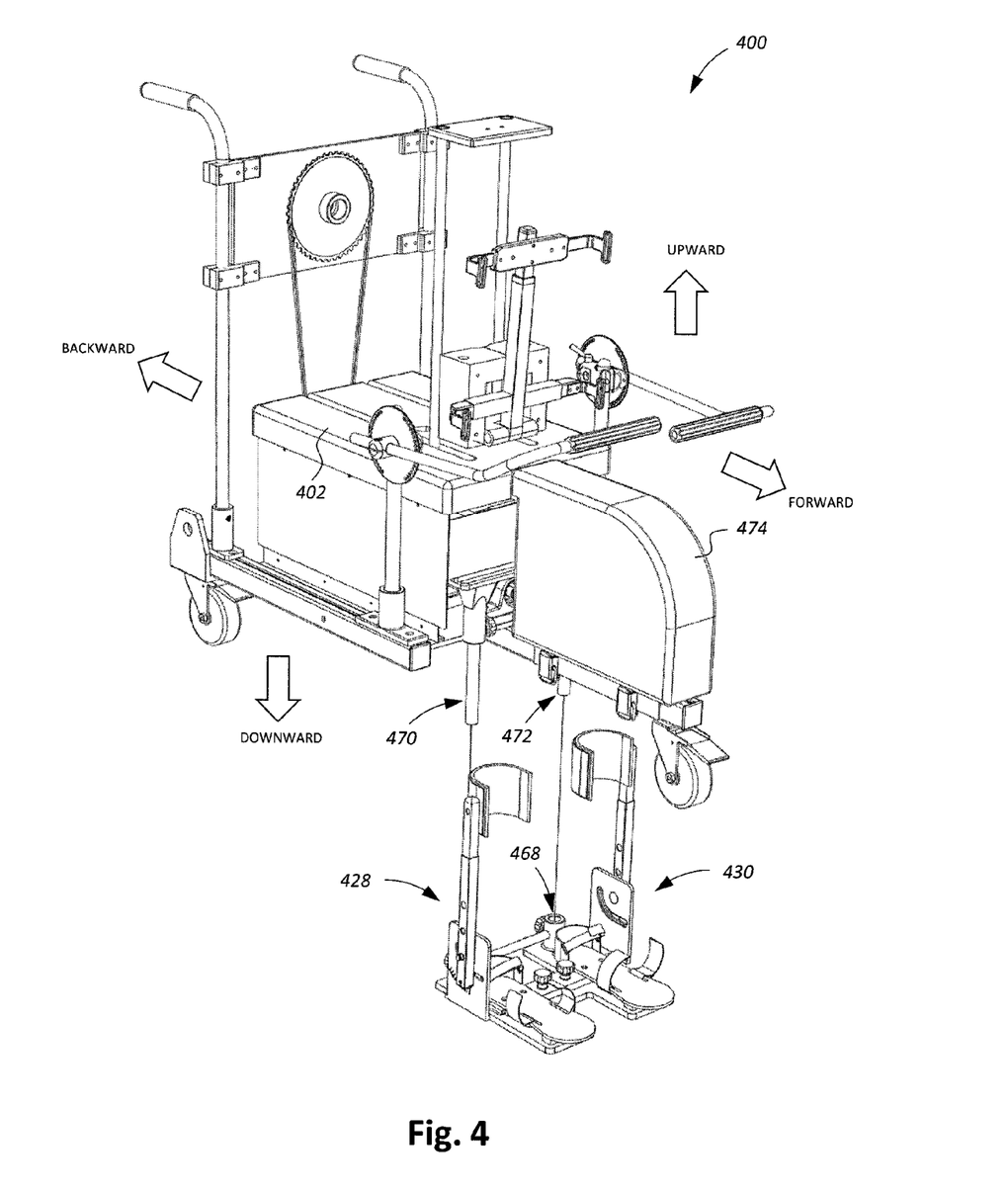
FIG. 4 shows a front perspective view of an exemplary orthotic apparatus, which may also serve as a combined chair, dynamic stander and walker for use by a motorically-limited user.

Reference is now made to FIG. 4, which show a front perspective view of an exemplary STS apparatus 400 (also referred to as an "orthotic apparatus", a "combined chair, dynamic stander and walker" or simply "apparatus"), in accordance with an alternative embodiment. Apparatus 400, in this embodiment, may include essentially the same elements of apparatus 100 (FIGS. 1A-B) and operate in accordance with the same principles of method 200 (FIG. 2), except with regard to those specific elements and principles discussed below as being different. For reasons of simplicity, elements of apparatus 400 which are identical to corresponding elements of apparatus 100 (FIGS. 1A-B), are not numbered in FIG. 4. In addition, it is explicitly intended that all of the above discussions will apply, mutatis mutandis, to apparatus 400.

Apparatus 400, different from apparatus 100 (FIGS. 1A-B), may be provided with detachable footrest assemblies 428-430, in lieu of footrests 128-130 and calf supports 132 (FIGS. 1A-B). Detaching footrest assemblies 428-430 from apparatus 400 (and placing them elsewhere) may allow the apparatus to be used also as a walker. Optionally, seat 402 may be lowered using a seat lowering mechanism of apparatus 400, such that, when the user sits, his or her feet can reach the ground. Then, the user may stand up and start walking. Namely, a user may use apparatus 400 both for sitting, for practicing STS, for standing and—when footrest assemblies 428-430 are detached—for walking, thereby propelling the apparatus over the ground. Optionally, one or more wheels of apparatus 400 may be equipped with a ratchet mechanism, allowing them to rotate only in one direction—forward. This may prevent apparatus 400 from moving backwards due to the user accidentally falling back.

Each of footrest assemblies 428-430 may include a footrest and a calf support, identical or similar to those of FIGS. 1A-B. However, each footrest may include a tube connector, such as tube connector 468, for mounting the footrest onto apparatus 400. A pair of poles, such as poles 470-472, may be connected to or integrally formed with apparatus 400, and be threaded through the tube connectors on respective sides.

When the user performs walking movements with his or her feet, apparatus 400 may travel along with the user (e.g. by sliding on wheels of the apparatus), due to the user being attached to the apparatus with the trunk harness.

Optionally, apparatus 400 includes a leg separator 474 for preventing the user's legs from being too close to each other or from crossing one another as the user walks. Leg separator 474 may be a plate aligned with the sagittal plane. Leg separator 474 may be no higher than a seat 402, such that the leg separator does not contact the user's crotch when standing. Optionally, at least a top part of leg separator 474 is cushioned, such that the user may comfortably sit on it to rest if reaching seat 402 is too difficult.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

What is claimed is:

1. An orthotic apparatus comprising:
   a seat;
   a trunk support movable horizontally and vertically relative to said seat, said trunk support configured to confine motion of a user to a predetermined range when the user independently transitions between sitting on said seat and standing, and vice versa, so as to guide the user in the transition; and
   one or more handles positioned forward of the seat, to guide the user to bring a center of gravity of the user forward during the transition, wherein said one or more handles are positioned at a height forcing the user to release a grip on said one or more handles during a body extension phase.

2. The orthotic apparatus according to claim 1, further comprising a weight compensator configured to compensate for a weight of said trunk support, so as to minimize interference of said trunk support with the transition of the user.

3. The orthotic apparatus according to claim 1, wherein said trunk support is further configured to cushion a fall of the user from standing to sitting.

4. The orthotic apparatus according to claim 1, wherein said trunk support is connected to a base of said orthotic apparatus using a polar fixation mechanism.

5. An orthotic apparatus comprising:
   a seat;
   a trunk support movable horizontally and vertically relative to said seat, said trunk support configured to confine motion of a user to a predetermined range when the user independently transitions between sitting on said seat and standing, and vice versa, so as to guide the user in the transition;
   a trunk column connected to a horizontal track beneath said seat; and
   a trunk harness attachable to the user and connected to said trunk column along a height of at least a portion of a trunk of the user.

6. The orthotic apparatus according to claim 5, further comprising a weight compensator configured to compensate for a weight of said trunk support, so as to minimize interference of said trunk support with the transition of the user.

7. The orthotic apparatus according to claim 5, wherein said trunk support is further configured to cushion a fall of the user from standing to sitting.

8. The orthotic apparatus according to claim 5, further comprising one or more footrests configured to secure one or more feet of the user, respectively, wherein said one or more footrests are detachable from said orthotic apparatus, thereby enabling use of said orthotic apparatus as a walker.

9. An orthotic apparatus comprising:
   a seat;
   a trunk support movable horizontally and vertically relative to said seat, said trunk support configured to confine motion of a user to a predetermined range when the user independently transitions between sitting on said seat and standing, and vice versa, so as to guide the user in the transition, wherein said trunk support comprises a fixation mechanism configured to affix the user in a standing posture;
   a trunk column; and
   a trunk harness attachable to the user and connected to said trunk column along a height of at least a portion of a trunk of the user.

10. The orthotic apparatus according to claim 9, further comprising a weight compensator configured to compensate for a weight of said trunk support, so as to minimize interference of said trunk support with the transition of the user.

11. The orthotic apparatus according to claim 9, wherein said trunk support is further configured to cushion a fall of the user from standing to sitting.

12. The orthotic apparatus according to claim 9, wherein said trunk support is connected to a base of said orthotic apparatus using a polar fixation mechanism.

13. The orthotic apparatus according to claim 9, further comprising one or more footrests configured to secure one or more feet of the user, respectively, wherein said one or more footrests are detachable from said orthotic apparatus, thereby enabling use of said orthotic apparatus as a walker.

14. An orthotic apparatus comprising:
   a seat;
   a trunk support movable horizontally and vertically relative to said seat, said trunk support configured to confine motion of a user to a predetermined range when the user independently transitions between sitting on said seat and standing, and vice versa, so as to guide the user in the transition; and
   one or more footrests configured to secure one or more feet of the user, respectively, wherein said one or more footrests are detachable from said orthotic apparatus, thereby enabling use of said orthotic apparatus as a walker.

15. The orthotic apparatus according to claim 14, further comprising one or more calf supports configured, together with said one or more footrests, to maintain the ankle and calf of each leg of the user in same sagittal planes, and the two legs being in parallel sagittal planes during the STS transitions.

16. The orthotic apparatus according to claim 14, wherein said one or more footrests are further configured to slide backwards upon a beginning of the transition between sitting on said seat and standing, thereby making the user enter a posture suitable for a flexion momentum phase of the transition between sitting on said seat and standing.

17. The orthotic apparatus according to claim 14, wherein said seat is further configured to slide forward upon a beginning of the transition between sitting on said seat and standing, thereby making the user enter a posture suitable for a flexion momentum phase of the transition between sitting on said seat and standing.

18. The orthotic apparatus according to claim 14, further comprising a weight compensator configured to compensate for a weight of said trunk support, so as to minimize interference of said trunk support with the transition of the user.

19. The orthotic apparatus according to claim 14, wherein said trunk support is further configured to cushion a fall of the user from standing to sitting.

20. The orthotic apparatus according to claim 14, wherein said trunk support is connected to a base of said orthotic apparatus using a polar fixation mechanism.

21. A dynamic stander, comprising:
   a dynamic supporting column having an adjustable height;
   a harness configured to:

connect a user along a height of at least a portion of the trunk of the user to the dynamic supporting column, and guide the user when the user independently transitions between a sitting position and a standing position; and one or more handles configured to guide the user to bring a center of gravity of the user forward during the transition, wherein said one or more handles are positioned at a height forcing the user to release a grip on said one or more handles during a body extension phase.

22. A dynamic stander, comprising:

a dynamic supporting column having an adjustable height;

a harness configured to:

connect a user along a height of at least a portion of the trunk of the user to the dynamic supporting column, and guide the user when the user independently transitions between a sitting position and a standing position; and one or more detachable footrests configured to:

a) secure one or more feet of the user, respectively, and b) slide backwards upon a beginning of the transition between the sitting position and the standing position, thereby making the user enter a posture suitable for a flexion momentum phase of the transition between the sitting position and the standing position.

23. The dynamic stander of claim 22, further comprising one or more calf supports configured, together with said one or more footrests, to maintain the ankle and calf of each leg of the user in same sagittal planes, and the two legs being in parallel sagittal planes during the transition.

* * * * *